(12) United States Patent
Youssef et al.

(10) Patent No.: US 8,034,081 B2
(45) Date of Patent: Oct. 11, 2011

(54) INTERSPINOUS DYNAMIC STABILIZATION IMPLANT AND METHOD OF IMPLANTING

(75) Inventors: Jim A. Youssef, Durango, CO (US); Jeffrey Chun Wang, Sherman Oaks, CA (US); Brian Hewko, Bay Village, OH (US); Alan W. Cannon, Sunnyvale, CA (US)

(73) Assignee: CollabComl, LLC, Durango, CO (US)

( * ) Notice: Subject to any disclaimer, the term of this patent is extended or adjusted under 35 U.S.C. 154(b) by 1283 days.

(21) Appl. No.: 11/703,328

(22) Filed: Feb. 6, 2007

(65) Prior Publication Data
US 2008/0234824 A1   Sep. 25, 2008

(51) Int. Cl.
*A61B 17/70* (2006.01)
*A61F 2/44* (2006.01)

(52) U.S. Cl. ..... 606/249; 606/248; 606/246; 623/17.16; 623/17.11

(58) Field of Classification Search .......... 606/105, 606/248–249, 279; 623/17.11–17.16
See application file for complete search history.

(56) References Cited

U.S. PATENT DOCUMENTS

| | | | |
|---|---|---|---|
| 4,611,582 A * | 9/1986 | Duff ............... 606/258 |
| 4,932,975 A | 6/1990 | Main et al. |
| 5,098,434 A | 3/1992 | Serbousek |
| 5,360,448 A | 11/1994 | Thramann |
| 5,645,599 A | 7/1997 | Samani |
| 5,672,175 A | 9/1997 | Martin |
| 5,683,391 A | 11/1997 | Boyd |
| 5,733,284 A | 3/1998 | Martin |
| 5,837,328 A | 11/1998 | Spearin et al. |
| 5,865,848 A | 2/1999 | Baker |
| 6,120,503 A | 9/2000 | Michelson |
| 6,136,001 A | 10/2000 | Michelson |
| 6,139,551 A | 10/2000 | Michelson et al. |
| 6,149,652 A | 11/2000 | Sucherman et al. |
| RE37,005 E | 12/2000 | Michelson et al. |
| 6,190,388 B1 | 2/2001 | Michelson et al. |
| RE37,161 E | 5/2001 | Michelson et al. |
| 6,364,880 B1 | 4/2002 | Michelson |
| 6,375,683 B1 * | 4/2002 | Crozet et al. ............... 623/17.15 |
| 6,395,033 B1 | 5/2002 | Pepper |

(Continued)

FOREIGN PATENT DOCUMENTS
FR   2 882 513   9/2006
(Continued)

*Primary Examiner* — Thomas C. Barrett
*Assistant Examiner* — Caitlyn Miller
(74) *Attorney, Agent, or Firm* — Alan W. Cannon; Law Office of Alan W. Cannon (57) ABSTRACT

Devices and methods for treating spinal disorders and associated discomfort therefrom. In one embodiment, an interspinous implant device is configured for distracting an adjacent pair of spinous processes while permitting relative flexion, lateral bending and side rotation motions between the vertebrae joined to the adjacent pair of spinous processes. A method of treating spinal disorders and associated discomfort therefrom, includes inserting an interspinous device between a pair of adjacent spinous processes such that a superior portion of the device contacts an inferior surface of the relatively superior spinous process of the pair, and an inferior portion of the of the device contacts a superior surface of the relatively inferior spinous process of the pair; and distracting the superior and inferior portions, relative to one another, thereby distracting the spinous processes, whereby vertebrae integral with the spinous processes retain capability of flexion, lateral bending and side rotation motions, relative to one another, after the distraction has been performed.

16 Claims, 7 Drawing Sheets

U.S. PATENT DOCUMENTS

| | | |
|---|---|---|
| 6,402,750 B1 | 6/2002 | Atkinson et al. |
| 6,443,987 B1 | 9/2002 | Bryan |
| 6,451,019 B1 | 9/2002 | Zucherman et al. |
| 6,514,256 B2 | 2/2003 | Sucherman et al. |
| 6,610,091 B1 | 8/2003 | Reiley |
| 6,626,909 B2 | 9/2003 | Chin |
| 6,652,527 B2 | 11/2003 | Zucherman et al. |
| 6,669,729 B2 | 12/2003 | Chin |
| 6,679,883 B2 | 1/2004 | Hawkes et al. |
| 6,682,530 B2 | 1/2004 | Dixon et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,730,092 B2 | 5/2004 | Songer |
| 6,743,257 B2 | 6/2004 | Castro |
| 6,761,720 B1 | 7/2004 | Senegas |
| 6,783,527 B2 | 8/2004 | Drewry et al. |
| 6,796,983 B1 | 9/2004 | Zucherman et al. |
| 6,811,567 B2 | 11/2004 | Reiley |
| 6,835,205 B2 | 12/2004 | Atkinson et al. |
| 6,835,207 B2 | 12/2004 | Zacouto et al. |
| 6,949,123 B2 | 9/2005 | Reiley |
| 6,966,910 B2 | 11/2005 | Ritland |
| 6,974,478 B2 | 12/2005 | Reiley et al. |
| 7,074,238 B2 | 7/2006 | Stinson et al. |
| 7,087,084 B2 | 8/2006 | Reiley |
| 7,682,376 B2* | 3/2010 | Trieu ............................ 606/248 |
| 7,811,327 B2* | 10/2010 | Hansell et al. ............. 623/17.15 |
| 2001/0027319 A1 | 10/2001 | Ferree |
| 2002/0007184 A1 | 1/2002 | Ogilvie et al. |
| 2002/0013586 A1 | 1/2002 | Justis et al. |
| 2002/0049444 A1 | 4/2002 | Knox |
| 2002/0077630 A1 | 6/2002 | Lin |
| 2002/0120269 A1 | 8/2002 | Lange |
| 2002/0120270 A1 | 8/2002 | Trieu et al. |
| 2002/0133155 A1 | 9/2002 | Ferree |
| 2002/0143329 A1 | 10/2002 | Serhan et al. |
| 2002/0143399 A1 | 10/2002 | Sutcliffe |
| 2002/0151896 A1 | 10/2002 | Ferree |
| 2002/0151978 A1* | 10/2002 | Zacouto et al. ............. 623/17.12 |
| 2002/0161367 A1 | 10/2002 | Ferree |
| 2002/0169451 A1 | 11/2002 | Yeh |
| 2002/0183754 A1 | 12/2002 | Michelson |
| 2002/0183755 A1 | 12/2002 | Michelson |
| 2002/0183756 A1 | 12/2002 | Michelson |
| 2002/0183757 A1 | 12/2002 | Michelson |
| 2002/0183847 A1 | 12/2002 | Lieberman |
| 2002/0188296 A1 | 12/2002 | Michelson |
| 2002/0198598 A1 | 12/2002 | Pepper |
| 2003/0004572 A1 | 1/2003 | Goble et al. |
| 2003/0014117 A1 | 1/2003 | Lambrecht et al. |
| 2003/0040746 A1 | 2/2003 | Mitchell et al. |
| 2003/0045877 A1 | 3/2003 | Yeh |
| 2003/0055426 A1 | 3/2003 | Carbone et al. |
| 2003/0055427 A1 | 3/2003 | Graf |
| 2003/0060828 A1 | 3/2003 | Michelson |
| 2003/0065329 A1 | 4/2003 | Vaughan |
| 2003/0065396 A1 | 4/2003 | Michelson |
| 2003/0078661 A1 | 4/2003 | Houfburg |
| 2003/0083658 A1 | 5/2003 | Hawkes et al. |
| 2003/0105459 A1 | 6/2003 | Songer |
| 2003/0135210 A1 | 7/2003 | Dixon et al. |
| 2003/0144665 A1 | 7/2003 | Munting |
| 2003/0144666 A1 | 7/2003 | Bagga et al. |
| 2003/0153912 A1 | 8/2003 | Graf |
| 2003/0163132 A1 | 8/2003 | Chin |
| 2003/0167091 A1 | 9/2003 | Scharf |
| 2003/0171753 A1 | 9/2003 | Collins et al. |
| 2003/0187435 A1 | 10/2003 | Lin |
| 2003/0187454 A1 | 10/2003 | Gill et al. |
| 2003/0191470 A1 | 10/2003 | Ritland |
| 2003/0191535 A1 | 10/2003 | Castro |
| 2003/0208273 A1 | 11/2003 | Eisermann et al. |
| 2003/0216736 A1 | 11/2003 | Robinson et al. |
| 2004/0002708 A1 | 1/2004 | Ritland |
| 2004/0006343 A1 | 1/2004 | Sevrain |
| 2004/0010254 A1 | 1/2004 | Cook et al. |
| 2004/0015166 A1 | 1/2004 | Gorek |
| 2004/0019353 A1 | 1/2004 | Freid et al. |
| 2004/0034251 A1 | 2/2004 | Hiyoshi et al. |
| 2004/0034353 A1 | 2/2004 | Michelson |
| 2004/0034356 A1 | 2/2004 | LeHuec et al. |
| 2004/0039387 A1 | 2/2004 | Gause et al. |
| 2004/0039448 A1 | 2/2004 | Pisharodi |
| 2004/0044409 A1 | 3/2004 | Alfaro et al. |
| 2004/0049190 A1 | 3/2004 | Biedermann et al. |
| 2004/0068318 A1 | 4/2004 | Coates et al. |
| 2004/0073214 A1 | 4/2004 | Mehdizadeh |
| 2004/0073215 A1 | 4/2004 | Carli |
| 2004/0073216 A1 | 4/2004 | Lieberman |
| 2004/0073313 A1 | 4/2004 | Link et al. |
| 2004/0078082 A1 | 4/2004 | Lange |
| 2004/0078085 A1 | 4/2004 | Pointillart et al. |
| 2004/0087948 A1 | 5/2004 | Suddaby |
| 2004/0087950 A1 | 5/2004 | Teitelbaum |
| 2004/0092939 A1 | 5/2004 | Freid et al. |
| 2004/0092993 A1 | 5/2004 | Teitelbaum et al. |
| 2004/0097925 A1 | 5/2004 | Boehm, Jr. et al. |
| 2004/0102846 A1 | 5/2004 | Keller et al. |
| 2004/0111161 A1 | 6/2004 | Trieu |
| 2004/0116927 A1 | 6/2004 | Graf |
| 2004/0116931 A1 | 6/2004 | Carlson |
| 2004/0122424 A1 | 6/2004 | Ferree |
| 2004/0127989 A1 | 7/2004 | Dooris et al. |
| 2004/0133281 A1 | 7/2004 | Khandkar et al. |
| 2004/0143266 A1 | 7/2004 | Kozak et al. |
| 2004/0147928 A1 | 7/2004 | Landry et al. |
| 2004/0158245 A1 | 8/2004 | Chin |
| 2004/0172131 A1 | 9/2004 | Michelson |
| 2004/0177847 A1 | 9/2004 | Foley et al. |
| 2004/0181223 A1 | 9/2004 | Ritland |
| 2004/0181225 A1 | 9/2004 | Songer |
| 2004/0181226 A1 | 9/2004 | Michelson |
| 2004/0181229 A1 | 9/2004 | Michelson |
| 2004/0181282 A1 | 9/2004 | Zucherman et al. |
| 2004/0181284 A1 | 9/2004 | Simonson |
| 2004/0186475 A1 | 9/2004 | Falahee |
| 2004/0186476 A1 | 9/2004 | Michelson |
| 2004/0186570 A1 | 9/2004 | Rapp |
| 2004/0186572 A1 | 9/2004 | Lange et al. |
| 2004/0193161 A1 | 9/2004 | Vaughan |
| 2004/0193271 A1 | 9/2004 | Fraser et al. |
| 2004/0199254 A1 | 10/2004 | Louis et al. |
| 2004/0210314 A1 | 10/2004 | Michelson |
| 2004/0220570 A1 | 11/2004 | Frigg |
| 2004/0225289 A1 | 11/2004 | Biedermann et al. |
| 2004/0225290 A1 | 11/2004 | Ferree |
| 2004/0230192 A1 | 11/2004 | Graf |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0243126 A1 | 12/2004 | Carbone et al. |
| 2004/0243239 A1 | 12/2004 | Taylor |
| 2004/0249377 A1 | 12/2004 | Kaes et al. |
| 2004/0249461 A1 | 12/2004 | Ferree |
| 2004/0254578 A1 | 12/2004 | Vaughan |
| 2004/0254643 A1 | 12/2004 | Jackson |
| 2004/0260396 A1 | 12/2004 | Ferree et al. |
| 2004/0267260 A1 | 12/2004 | Mack et al. |
| 2005/0004674 A1 | 1/2005 | Senegas et al. |
| 2005/0010292 A1 | 1/2005 | Carrasco |
| 2005/0010296 A1 | 1/2005 | Mitchell |
| 2005/0010298 A1 | 1/2005 | Zucherman et al. |
| 2005/0015146 A1 | 1/2005 | Louis et al. |
| 2005/0021031 A1 | 1/2005 | Foley et al. |
| 2005/0027296 A1 | 2/2005 | Thramann et al. |
| 2005/0027297 A1 | 2/2005 | Michelson |
| 2005/0027298 A1 | 2/2005 | Michelson |
| 2005/0027360 A1 | 2/2005 | Webb et al. |
| 2005/0027362 A1 | 2/2005 | Williams et al. |
| 2005/0033291 A1 | 2/2005 | Ebara |
| 2005/0033294 A1 | 2/2005 | Garden et al. |
| 2005/0033298 A1 | 2/2005 | Hawkes et al. |
| 2005/0033431 A1 | 2/2005 | Gordon et al. |
| 2005/0033432 A1 | 2/2005 | Gordon et al. |
| 2005/0033434 A1 | 2/2005 | Berry |
| 2005/0033439 A1 | 2/2005 | Gordon et al. |

| | | |
|---|---|---|
| 2005/0038432 A1 | 2/2005 | Shaolian et al. |
| 2005/0038434 A1 | 2/2005 | Mathews |
| 2005/0038516 A1 | 2/2005 | Spoonamore |
| 2005/0043797 A1 | 2/2005 | Lee |
| 2005/0043800 A1 | 2/2005 | Paul et al. |
| 2005/0043803 A1 | 2/2005 | Schultz et al. |
| 2005/0043804 A1 | 2/2005 | Gordon et al. |
| 2005/0049595 A1 | 3/2005 | Suh et al. |
| 2005/0049708 A1 * | 3/2005 | Atkinson et al. ............ 623/17.16 |
| 2005/0055025 A1 | 3/2005 | Zacouto et al. |
| 2005/0055029 A1 | 3/2005 | Marik et al. |
| 2005/0055098 A1 | 3/2005 | Zdeblick et al. |
| 2005/0060034 A1 | 3/2005 | Berry et al. |
| 2005/0060035 A1 | 3/2005 | Errico et al. |
| 2005/0060036 A1 | 3/2005 | Schultz et al. |
| 2005/0065514 A1 | 3/2005 | Studer |
| 2005/0065610 A1 | 3/2005 | Pisharodi |
| 2005/0065611 A1 | 3/2005 | Huppert et al. |
| 2005/0070900 A1 | 3/2005 | Serhan et al. |
| 2005/0070901 A1 | 3/2005 | David |
| 2005/0070908 A1 | 3/2005 | Cragg |
| 2005/0070913 A1 | 3/2005 | Milbocker et al. |
| 2005/0075634 A1 | 4/2005 | Zucherman et al. |
| 2005/0080420 A1 | 4/2005 | Farris et al. |
| 2005/0080487 A1 | 4/2005 | Schultz et al. |
| 2005/0080488 A1 | 4/2005 | Schultz |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085909 A1 | 4/2005 | Eisermann |
| 2005/0085911 A1 | 4/2005 | Link |
| 2005/0085914 A1 | 4/2005 | Lange et al. |
| 2005/0085917 A1 | 4/2005 | Marnay et al. |
| 2005/0090900 A1 | 4/2005 | Nordquist |
| 2005/0096657 A1 | 5/2005 | Autericque et al. |
| 2005/0096746 A1 | 5/2005 | Bryan et al. |
| 2005/0102029 A1 | 5/2005 | Blain |
| 2005/0107880 A1 | 5/2005 | Shimp et al. |
| 2005/0113916 A1 | 5/2005 | Branch |
| 2005/0113924 A1 | 5/2005 | Buttermann |
| 2005/0113927 A1 | 5/2005 | Malek |
| 2005/0113929 A1 | 5/2005 | Cragg et al. |
| 2005/0119749 A1 | 6/2005 | Lange |
| 2005/0125029 A1 | 6/2005 | Bernard et al. |
| 2005/0125063 A1 | 6/2005 | Matge et al. |
| 2005/0131406 A1 | 6/2005 | Reiley et al. |
| 2005/0131409 A1 | 6/2005 | Chervitz et al. |
| 2005/0131536 A1 | 6/2005 | Eisermann et al. |
| 2005/0131537 A1 | 6/2005 | Hoy et al. |
| 2005/0131539 A1 | 6/2005 | Kohrs |
| 2005/0137594 A1 | 6/2005 | Doubler et al. |
| 2005/0137596 A1 | 6/2005 | Uwaydah |
| 2005/0143737 A1 | 6/2005 | Pafford et al. |
| 2005/0143818 A1 | 6/2005 | Yuan et al. |
| 2005/0143823 A1 | 6/2005 | Boyd et al. |
| 2005/0143825 A1 | 6/2005 | Enayati |
| 2005/0149023 A1 | 7/2005 | Ritland |
| 2005/0149188 A1 | 7/2005 | Cook et al. |
| 2005/0149189 A1 | 7/2005 | Mokhtar et al. |
| 2005/0149190 A1 | 7/2005 | Reiley |
| 2005/0149191 A1 | 7/2005 | Cragg et al. |
| 2005/0149194 A1 | 7/2005 | Ahlgren |
| 2005/0149195 A1 | 7/2005 | Boyd et al. |
| 2005/0149196 A1 | 7/2005 | Zucherman et al. |
| 2005/0154390 A1 | 7/2005 | Biedermann et al. |
| 2005/0154459 A1 | 7/2005 | Wolek et al. |
| 2005/0154461 A1 | 7/2005 | Humphreys et al. |
| 2005/0154462 A1 | 7/2005 | Zucherman et al. |
| 2005/0154464 A1 | 7/2005 | Humphreys et al. |
| 2005/0154465 A1 | 7/2005 | Hodges et al. |
| 2005/0154466 A1 | 7/2005 | Humphreys et al. |
| 2005/0154467 A1 | 7/2005 | Peterman et al. |
| 2005/0159813 A1 | 7/2005 | Molz |
| 2005/0159814 A1 | 7/2005 | Karahalios |
| 2005/0159815 A1 | 7/2005 | Kamimura et al. |
| 2005/0159818 A1 | 7/2005 | Blain |
| 2005/0165396 A1 | 7/2005 | Fortin et al. |
| 2005/0165407 A1 | 7/2005 | Diaz |
| 2005/0165485 A1 | 7/2005 | Trieu |
| 2005/0165486 A1 | 7/2005 | Trieu |
| 2005/0165487 A1 | 7/2005 | Muhanna et al. |
| 2005/0171550 A1 | 8/2005 | Marik |
| 2005/0171554 A1 | 8/2005 | Estes et al. |
| 2005/0171605 A1 | 8/2005 | Link et al. |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0187548 A1 | 8/2005 | Butler et al. |
| 2005/0203517 A1 | 9/2005 | Jahng et al. |
| 2005/0203518 A1 | 9/2005 | Biedermann et al. |
| 2005/0203624 A1 * | 9/2005 | Serhan et al. ............... 623/17.11 |
| 2005/0209694 A1 | 9/2005 | Loeb |
| 2005/0216004 A1 | 9/2005 | Schwab |
| 2005/0216010 A1 | 9/2005 | Michelson |
| 2005/0222569 A1 | 10/2005 | Panjabi |
| 2005/0240266 A1 | 10/2005 | Kuiper et al. |
| 2005/0277930 A1 | 12/2005 | Parsons |
| 2005/0288670 A1 | 12/2005 | Panjabi et al. |
| 2006/0004447 A1 | 1/2006 | Mastrorio et al. |
| 2006/0036240 A1 * | 2/2006 | Colleran et al. ................. 606/61 |
| 2006/0084988 A1 | 4/2006 | Kim |
| 2006/0235521 A1 | 10/2006 | Zucherman et al. |
| 2006/0241601 A1 | 10/2006 | Trautwein et al. |
| 2006/0241610 A1 | 10/2006 | Lim et al. |
| 2006/0247635 A1 | 11/2006 | Gordon et al. |
| 2006/0247640 A1 | 11/2006 | Blackwell et al. |
| 2006/0265067 A1 | 11/2006 | Zucherman et al. |
| 2006/0293662 A1 | 12/2006 | Boyer, II et al. |
| 2007/0005064 A1 | 1/2007 | Anderson et al. |
| 2007/0016303 A1 | 1/2007 | Jackson |
| 2008/0249528 A1 * | 10/2008 | Khalife ........................... 606/90 |

FOREIGN PATENT DOCUMENTS

| | | |
|---|---|---|
| FR | 2 888 744 | 1/2007 |
| FR | 2888744 A1 * | 1/2007 |
| WO | WO 98/29047 | 7/1998 |

* cited by examiner

INTERSPINOUS DYNAMIC STABILIZATION IMPLANT AND METHOD OF IMPLANTING

BACKGROUND OF THE INVENTION

With the aging of the population there has occurred an increase in the incidences of degenerative diseases of the spine and this trend is expected to continue with the continuing increase in the percentage of elderly people in the population. Spinal stenosis is one of the most frequent forms of spinal degenerative disease observed. One conventional treatment of spinal stenosis has been laminectomy and decompression of neurologic structures and fusing the treated vertebrae if instability exists. Many potentially negative side effects are inherent in this form of treatment, including profuse bleeding, substantial risk of infection, potential nerve damage sometimes leading to paralysis and/or bladder/bowel dysfunction, dural tears, persistent fluid leakage, arachnoiditis, continuing chronic pain, non-union (if fusion is performed), fusion hardware failure, donor site pain, adjacent segment disease, long operation times, and substantial operation costs.

There are inherent general risks of the surgical procedure and medical risks including, but not limited to: bleeding, infection, nerve or vessel damage, risks of anesthesia, death, need for further surgery, iatrogenic instability, epidural hematoma, failure or implants and/or associated hardware, misplacement of implants and hardware, migration of implants and hardware, heart attack, stroke, deep venous thrombosis, pulmonary embolism, spinal cord and nerve damage, reflex sympathetic dystrophy, sexual dysfunction, positioning problems, brachial plexus injuries, traction injuries, swallowing difficulties, problems with vocal cords, airway obstruction, postoperative swelling, need for prolonged intubation, persistent dural fistula, paralysis, blindness, no relief of current symptoms, possible development of new symptoms, possible worsening of current symptoms, possible need for intraoperative change of procedure, possible need for fusion of the spine as determined intraoperatively, and other rare risks not named above. The need for fusion of the spine can be sometimes first recognized intraoperatively, when a spinal fusion was not originally planned to be performed, but when instability or iatrogenic instability is encountered during the procedure that would make the spine unstable if the fusion were not performed. The risks, benefits, alternatives and risks of the alternatives are discussed with the patient, so that the patient understands the risks of the procedure to be performed and elects to proceed.

Other types of implants have been developed to distract the spinous processes without the performance of laminectomy or fusion to increase the space for existing nerves to thereby relieve pain. Implantation of these implants typically require a large incision and dissection on both sides of the spinous processes. Multiple steps of dilation and distraction are performed prior to implantation of the implant in order to final provide a sufficient interspinous space to wedge the implant between the spinous processes. Examples of implants of these types are described in U.S. Pat. Nos. 5,645,599; 6,149,652; 6,514,256; 6,695,842; and 6,761,720. Further, many of these devices are rigid, inflexible and non-adjustable wedge-like implants that require dissection of muscle tissue and/or ligaments such as the supraspinous ligament and interspinous ligament.

In view of these and other drawbacks with using currently existing spine treatments and inter-spinous implants, there is a continuing need for improved procedures and implants to treat disorders of the spine and pain associated therewith, and particularly for treatment of degenerative spine disorders, in the elderly as well as in any other vertebrate patients. It would be further advantageous to provide implants that are implantable via minimally invasive procedures, to reduce trauma, risks of infection and costs relative to those associated with currently available procedures. Still further, it would be desirable to provide such implants to be removable (i.e., explanted), if desired, by minimally invasive procedures. The ability to adjust the amount of distraction between the spinous processes, both during initial implantation and at a later time after completion of the implantation procedure, would also be desirable.

SUMMARY OF THE INVENTION

The present invention provided devices and methods for treating spinal disorders and associated discomfort therefrom.

In at least one embodiment, an interspinous implant device for distracting an adjacent pair of vertebrae while permitting relative flexion, lateral bending and side rotation motions between the vertebrae of the adjacent pair is provided, including: an inferior mount body configured to mate with a spinous process of the vertebra that is inferior, relative to the pair; a superior mount body configured to mate with a spinous process of a spinous process of the vertebra that is superior, relative to the vertebra that is inferior; and an intermediate member mounted intermediate of said inferior mount body and said superior mount body; wherein upon implantation of said device between the spinous processes to contact the spinous processes, said superior mount body and inferior mount body are movable in flexion, lateral bending and side rotation, relative to one another.

In at least one embodiment, the intermediate member is axially adjustable to adjust an amount of separation between the inferior mount body and the superior mount body.

In at least one embodiment, the intermediate member comprises a telescoping member.

In at least one embodiment, the telescoping member is slidably mounted over a superiorly extending shaft portion of the inferior mount body.

In at least one embodiment, a spacer is insertable to contact the intermediate member to alter a distance between the superior mount body and the inferior mount body.

In at least one embodiment, the spacer is removable from contact with the intermediate member, wherein a second spacer having a second thickness different from a first thickness of the spacer having been removed, is insertable to alter the distance between the superior and inferior mount bodies.

In at least one embodiment, a spacer is provided that is insertable to contact a telescoping member to drive telescoping of the telescoping member to alter a distance between the superior mount body and the inferior mount body.

In at least one embodiment, a locking mechanism is provided to releasably lock the spacer to the superiorly extending shaft portion of the inferior mount body.

In at least one embodiment, a guiding feature is provided to guide alignment of a spacer and a superiorly extending shaft portion of the inferior mount body, to align components of a locking mechanism.

In at least one embodiment, the guiding feature comprises flats on the superiorly extending shaft portion of the inferior mount body, and mating flat inner surfaces on the spacer.

In at least one embodiment, the spacer is removable from contact with the telescoping member, wherein a second spacer having a second thickness different from a first thickness of the spacer having been removed, is insertable to contact the telescoping member and alter the distance between the superior and inferior mount bodies.

In at least one embodiment, a dampening member is mounted on the intermediate member in a location to be contacted by a movement of one of the superior and inferior mount bodies prior to a limit of a range of motion of the superior or inferior mount body being reached, relative to said intermediate member.

An interspinous implant device for distracting an adjacent pair of spinous processes while permitting relative flexion, lateral bending and side rotation motions between the vertebrae joined to the adjacent pair of spinous processes is provided, including: an inferior mount body configured to mate with a relatively inferior spinous process of the pair; a superior mount body configured to mate with a relatively superior spinous process of the pair; and a joint intermediate of the inferior mount body and the superior mount body; wherein upon implantation of the device between the spinous processes to contact the spinous processes, the joint facilitates relative tilting and rotation movements between the superior mount body and the inferior mount body.

A method of treating spinal disorders and associated discomfort therefrom is provided including the steps of: inserting an interspinous device between a pair of adjacent spinous processes such that a superior portion of the device contacts an inferior surface of the relatively superior spinous process of the pair, and an inferior portion of the of the device contacts a superior surface of the relatively inferior spinous process of the pair; and distracting the superior and inferior portions, relative to one another, thereby distracting the spinous processes, whereby vertebrae integral with the spinous processes retain capability of flexion, lateral bending and side rotation motions, relative to one another, after the distracting has been performed.

In at least one embodiment, the inserting comprises advancing the device in an anterior direction through an incision aligned with the spinous processes.

In at least one embodiment, the spinous processes are distracted with a distraction tool, prior to inserting the device.

In at least one embodiment, the distracting comprises inserting a spacer intermediate of the superior and inferior portions of the device, thereby altering a distance between the superior and inferior portions.

In at least one embodiment, the spacer is locked to a portion of the device, relative to the superior and inferior portions.

In at least one embodiment, the method is performed as a minimally invasive procedure.

In at least one embodiment, the device is inserted in a collapsed configuration where superior and inferior ends are in an undistracted state. In at least one embodiment a device is implanted between a first pair of adjacent spinous processes, and the method further includes inserting a second interspinous device between a second pair of adjacent spinous processes such that a superior portion of the device contacts an inferior surface of the relatively superior spinous process of the second pair, and an inferior portion of the device contacts a superior surface of the relatively inferior spinous process of the second pair, and wherein the second pair of adjacent spinous processes includes one spinous process in common with the first pair of adjacent spinous processes.

In at least one embodiment, a device is implanted between a first pair of adjacent spinous processes, and a second pair of adjacent spinous processes extend from a pair of adjacent vertebrae having been fused, wherein the second pair of adjacent spinous processes includes one spinous process in common with the first pair of adjacent spinous processes.

These and other features of the invention will become apparent to those persons skilled in the art upon reading the details of the devices and methods as more fully described below.

DETAILED DESCRIPTION OF THE INVENTION

Before the present devices and procedures are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a spacer" includes a plurality of such spacers and reference to the "process" includes reference to one or more processes and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Vertebral Anatomy

Figure 1:
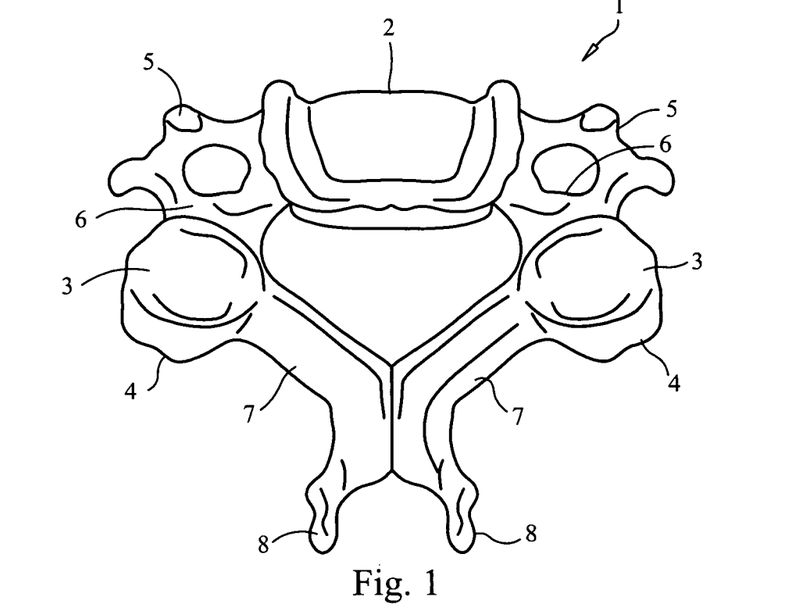
FIG. 1 is a superior view of a vertebra.

FIG. 1 is a superior view of a vertebra 1. The vertebral body 2 is an anterior portion of the vertebra and is somewhat cylindrical in shape. The intervertebral disks (not shown) are interposed between adjacent vertebral bodies in the spine. Each vertebra has two sets of facet joints 3,4, at posterior locations. One pair faces upward (superior articular facets 3) and one downward (inferior articular facets 4). There is one joint on each side (right and left). Facet joints are hinge-like and link vertebrae together. A transverse process 5 and pedicle 6 are located between the facets 3,4 and the vertebral body 2. The transverse processes 5 serve for the attachment of muscles and ligaments. The laminae 7 are plates of bone that form the posterior walls of each vertebra 2, enclosing the spinal cord or neural elements. The spinous process 8 is directed backward and downward from the junction of the laminae 7, and serves for the attachment of muscles and ligaments. In the cervical vertebrae, the spinous process 8 is often bifurcated, such as in the example shown in FIG. 1.

Figure 2:
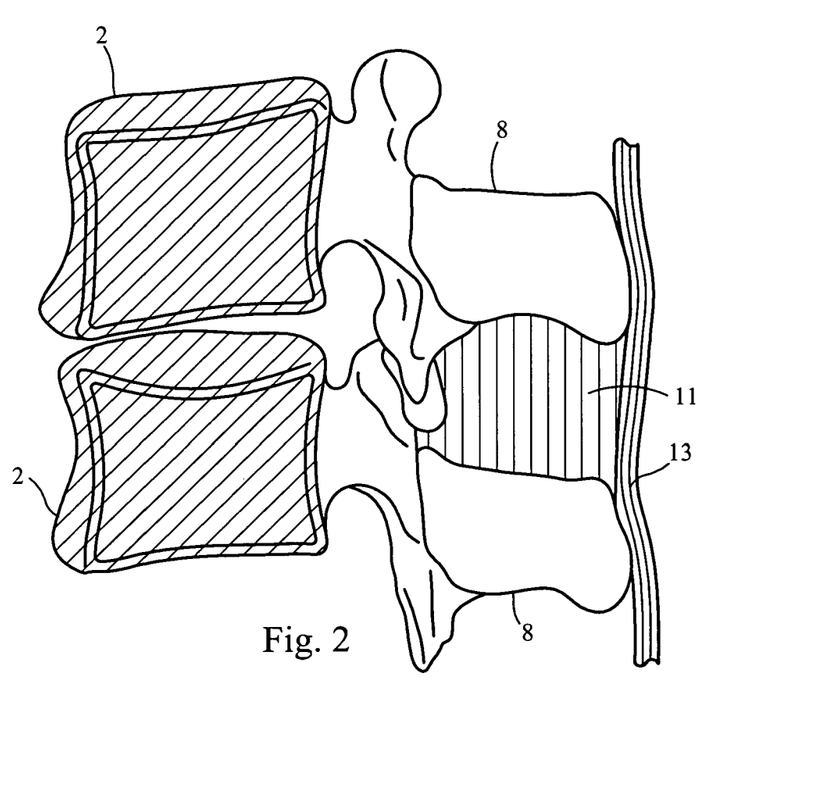
FIG. 2 is an illustration showing a lateral view of adjacent spinous processes and a sectional view of the vertebral bodies from the lumbar portion of the spine.

FIG. 2 is an illustration showing a lateral view of adjacent spinous processes 8,8 and a sectional view of the vertebral bodies 2 from the lumbar portion of the spine. FIG. 2 further illustrates interspinous ligament 11 and supraspinous ligament 13. Interspinous ligament 11 connects the adjacent spinous processes and stretches vertically from the inferior border of the upper spinous process 8 shown to the superior border of the adjacent spinous process 8 below. Interspinous ligament 11 interconnects adjacent spinous processes 8 in this manner with respect to all vertebrae, except those in the cervical spine, where it is absent. Supraspinous ligament 13 extends along the posterior tips of the spinous processes 8 and blends with the ligamentum nuchae at its superior end. In elderly individuals and in persons who engage in heavy physical activity, the ligament can become ossified, making a midline approach to the epidural space impossible.

Devices, Tools, Systems and Procedures

Figure 3:
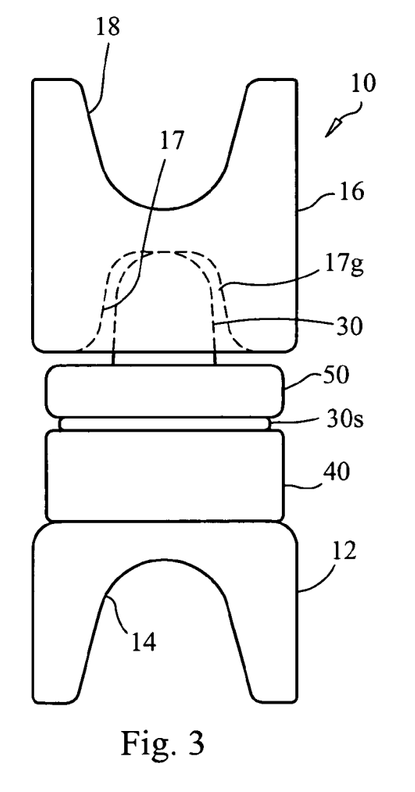
FIG. 3 is a posterior view of one embodiment of a device according to the present invention.

FIG. 3 shows an embodiment of an interspinous dynamic stabilization implant device 10 according to the present invention. Device 10 includes an inferior mount body 12 having a recessed inferior surface 14 configured and dimensioned to be mounted superiorly over a spinous process 8. Recessed inferior surface 14 may be saddle-shaped, or have another concave surface configuration or be otherwise recessed to form a congruent interface with a superior portion of the lower spinous process 8 when positioned between adjacent spinous processes 8 as described herein, or at least to provide a contact surface with lateral portions that prevent lateral escape of the spinous process 8 from contact with the inferior surface 14. Similarly, superior mount body 16 is provided with a recessed superior surface 18 configured and dimensioned to be mounted inferiorly against the spinous process 8 that is superiorly adjacent to the spinous process 8 over which inferior mount body is mounted. Recessed superior surface 18 may be saddle-shaped, or have another concave surface configuration or be otherwise recessed to form a congruent interface with the spinous process 8 or at least to provide a contact surface with lateral portions that prevent lateral escape of the spinous process 8 from contact with the superior surface 18.

Figure 4A:
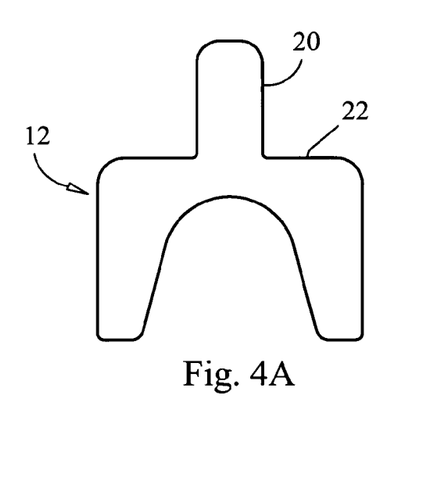
FIG. 4A is an isolated view of inferior mount body.
Figure 4B:
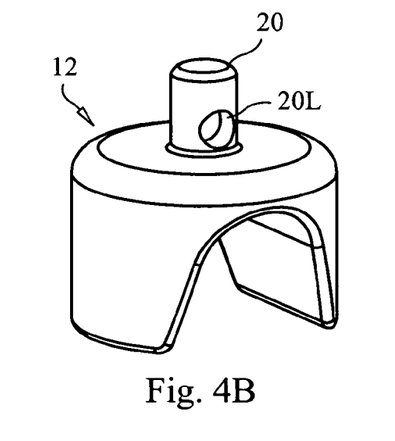
FIG. 4B illustrates a variation of the inferior mount body of FIG. 4A.

FIG. 4A is an isolated view of inferior mount body 12. Shaft or column 20 extends vertically (superiorly) from a superior surface 22 of inferior mount 12 and is configured to receive a telescoping member 30 thereover, so that telescoping member is free to slide with respect to the longitudinal axis of shaft/column 20 as well as rotate about shaft/column 20. FIG. 4B illustrates a variation of the inferior mount body 12 of FIG. 4A, in which shaft/column 20 includes a component 20L of a locking structure that may be provided, as discussed in greater detail below.

Figure 5A:
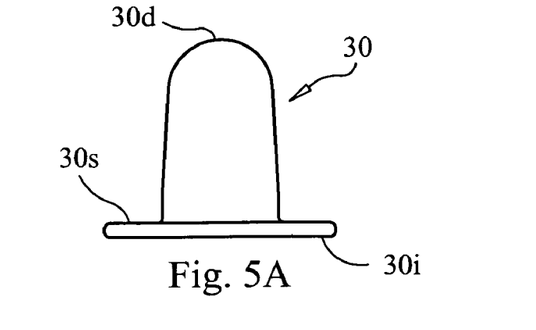
FIG. 5A illustrates an isolated view of a telescoping member.
Figure 5B:
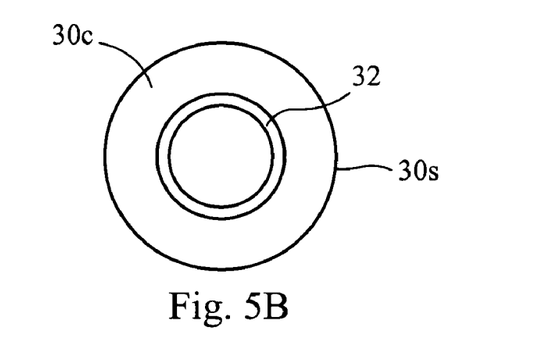
FIG. 5B illustrates a bottom view of the telescoping member of FIG. 5A.

Telescoping member 30 is shown in FIGS. 5A-5B and is provided as an elongated, rigid member having an annular space/opening 32 (FIGS. 5B,5C) extending though a majority thereof that is sized and dimensioned to permit telescoping member 30 to telescope (e.g., slide) over and with respect to shaft/column 20. The superior end of telescoping member 30 is typically, though not necessarily, closed to provide a greater bearing surface 30$d$ (relative to a telescoping member having an opening in the superior end) against which the recessed inferior surface 17 of superior mount body 16 articulates. When closed, the superior end may be spherical or have some other convex surface that forms the bearing surface 30$d$. The annular opening 32 has a diameter slightly greater than the outside diameter of shaft/column 20, but only slightly so, to provided tolerance to provide free telescoping ability, while at the same time preventing rocking or wobbling of telescoping member 30 with respect to shaft/column 20. Ranges of distraction that can be applied by device 10 will vary depending upon the location in the spine where device 10 is to be implanted, the sex of the patient, the age of the patient (e.g., pediatric vs. adult) and various other factors. In at least one embodiment device 10 is extendable from about 15 mm to about 30 mm (measured from the closest points between surfaces 14 and 18 in the cephelad caudal direction. For use in a cervical spine location, this range may be from about 15 mm to about 21 mm for example, whereas in the lumbar region, the range may be from about 18 mm to about 30 mm, although these ranges may vary depending upon a number of factors, some of which were identified above. The diameter of device

10 may also vary depending upon these same factors, and, for example, may range from about 12 mm to about 20 mm in at least one embodiment.

Figure 5C:
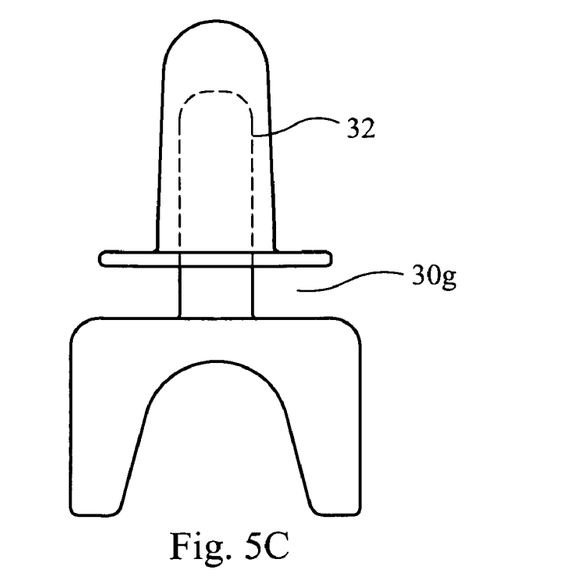
FIG. 5C shows the telescoping member of FIG. 5A mounted on the shaft or column of an inferior mount body.

If no spacer 40 has been inserted between telescoping member 30 and inferior mount body 12, annular space 32 will have insufficient length to allow the inferior surface 30i of telescoping member 30 to contact superior surface 22. That is, the superior end of shaft/column 20 contacts the superior end of annular space 32 before inferior surface 30i can contact surface 22, as illustrated in FIG. 5C. The gap 30g that remains when the superior end of annular space 32 has "bottomed out" against the superior end of shaft/column 20 can facilitate the application of a spacer 40, as described further below. Gap 30g is typically at least about 0.5 mm, but may be greater than this.

The inferior end portion of telescoping member 30 includes a lip or shoulder 30s that extends radially outwardly from the outer surface of telescoping member 30. Lip or shoulder 30s serves to support cushioning and/or dampening member 50 and prevent it from being driven off the inferior end of telescoping member 30. Although shown at the inferior end of telescoping member 30, it is noted that lip/shoulder 30s could be formed somewhat superiorly of the inferior end of telescoping member 30, although still in the location of the inferior end portion of telescoping member 30 (e.g., typically no higher than midway between inferior and superior surfaces).

Figure 6A:
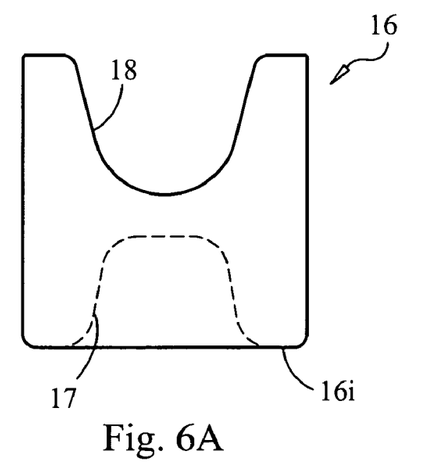
FIG. 6A is an isolated view of a superior mount body.
Figure 6B:
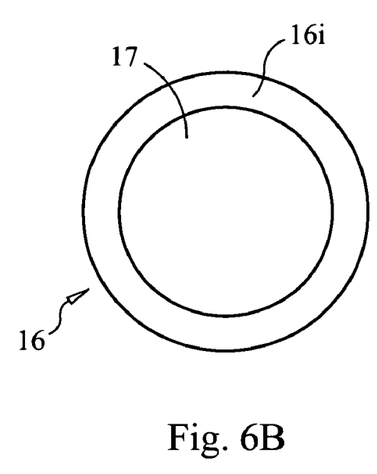
FIG. 6B is an inferior end view of the superior mount body shown in FIG. 6A.
Figure 7:
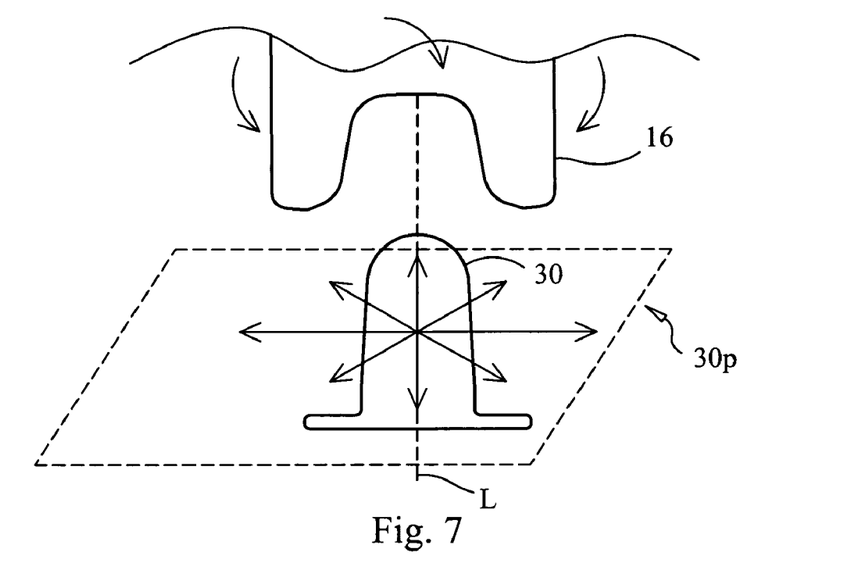
FIG. 7 illustrates the tiltability of superior mount body relative to telescoping member in all directions, 360 degrees about the longitudinal axis of the telescoping member.

FIG. 6A is an isolated view of superior mount body 16 and FIG. 6B is an inferior end view of the same. Recessed inferior surface extends superiorly and radially inwardly from the inferior surface 16i superior mount body 16 located at that inferior end of superior mount body 16, to form an opening or elongated recess into which telescoping member is received. Rather that forming a saddle shape, recessed inferior surface extends circumferentially within superior mount body to form a socket. FIG. 6B illustrates the circular opening formed where recessed inferior surface meets inferior surface 16i. In at least one embodiment, the external surface of at least the superior end portion of telescoping member is bell-shaped or having other parabolic curvature. Alternatively the external surface may be semi-spherical and joining a substantially cylindrical shaft. Likewise recessed inferior surface 17 can be bell shaped, but with a larger diameter that the corresponding diameter of telescoping member, at all adjacent respective locations where inferior surface 17 surrounds telescoping member 30. With such an arrangement, superior mount body 16 is permitted to rock or tilt with respect to telescoping member 30, articulating on the contact between inferior surface and the superior end surface of telescoping member 30. Tilting can be in any direction three hundred and sixty degrees around the longitudinal axis of telescoping member 30, as illustrated by the exemplary directional arrows on the imaginary plane 30p in FIG. 7. That is, superior mount body 16 can tilt in any plane passing though the longitudinal axis L of the telescoping member 30. Additionally, superior mount body is free to rotate with respect to telescoping member, about the longitudinal axis of superior mount body 16. Thus, upon implantation, device 10 allows motion in all directions and planes. Specifically, when implanted between two spinous processes 8 in a manner described herein, device 10 permits the following motions to be retained between the two vertebrae that are connected to the spinous processes 8 between which device 10 is implanted: flexion, lateral bending, and side rotation in each direction. Further device 10 prevents extension with a soft stop based on the dynamic nature of the device as described herein, and wherein the amount of extension is further limited. Although the amount of distraction is maintained by device 10 once properly positioned between the spinous processes 8, extension is limited in a dynamic fashion, coming to a hard stop once the full amount of compression through device 10 is realized. With regard to rotation, there exists a soft stop as well, as device 10 has some articulation allowing some level of rotation.

As noted above, telescoping member 30 need not have a bell or parabolic outer surface shape, but can alternatively be a straight shaft for example. Recessed inferior surface 17 may also have other shapes, but what needs to be maintained is a circumferential gap 17g around telescoping member 30 (between telescoping member 30 and inferior surface 17 when superior mount body 16 is mounted on telescoping member 30 as shown in FIG. 3A), that permits a sufficient degree of tilting of superior mount body 16 with respect to telescoping member 17. The gap 17g between the inferior end of superior mount body 16 and telescoping member 30 should be at least as wide as the gap 17g at all locations superior thereof, and may be greater. For example, gap 17g may progressively widen from its superior origination location to the inferior end adjacent the inferior end 16i of superior mount body 16. As another example, gap 17g may be defined by two spherical surfaces that remain tangent throughout flexion, extension and axial movements of the device 10. The space between these convex and concave surfaces may range from between about 0.5 mm and about 5 mm depending on the implantation location, and other factors described above. For use in the cervical spine, there may be a larger gap, e.g., about 3 mm to about 5 mm to allow for relatively greater medial/lateral bending, whereas, for use in a lumbar spine location, the gap may be smaller to facilitate supporting a much increase load, relative to that experienced in the cervical spine location. The amount of tilting allowed by superior mount body 16 relative to telescoping member 30 will also vary, depending on the factors already described, and on the size of gap 17g, thickness of collar 50, etc. For example, this range may be from about seven degrees to about twelve degrees, although this range may vary.

The flexion and extension dynamically permitted by device 10 may be about five mm and are typically amounts at least as great as about one to two mm.

The amount of tilting of superior mount body 16 with respect to telescoping member 30 may be limited by contact between recessed inferior surface 17 with telescoping member 30 in the vicinity of the inferior end of superior mount body 16. Alternatively, tilting motion may be stopped by contact between inferior surface 16i, spacer 50 and shoulder 30s and/or spacer 40. Further alternatively, the stop may be provided by a combination of these actions, with spacer 40 providing a dampening function and the hard surfaces of inferior surface 16i and shoulder 30s and/or spacer 50 forming a hard stop. In any case, spacer 50 may be formed of a compressible, elastomeric material, such as polyethylene, poly ether ether ketone (PEEK) having soft yield properties relative to the range of yield properties available in PEEK products, or other relatively soft, biocompatible polymers, to cushion the contact between inferior surface 16i with shoulder 30s and/or spacer 40, to make a smoother stop function, prevent noise from contact between two hardened components, reduce abrasion and wear between the hardened components and to refine the functionality of the device 10 in general. In order to further soften the stopping action of the device, spacer 50 may additionally provide dampening, thereby slowing the tilting action progressively upon contact and until the end stopping location as reached. For example, spacer 50 may be made from a viscoelastic polymer foam. The thickness of spacer 50 will vary, depending on the ranges of motion for the particular device 10, the location of the spine in which device 10 is to be implanted, the size and age of the patient (e.g., female vs. male, pediatrics vs. adult, etc.) and possibly other factors. In general the thickness may range from about two mm to about ten mm, but this may vary, as noted.

Figure 8A:
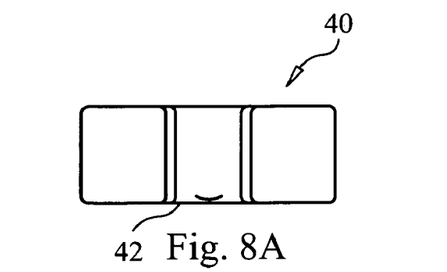
FIG. 8A illustrates an anterior view of a spacer.
Figure 8B:
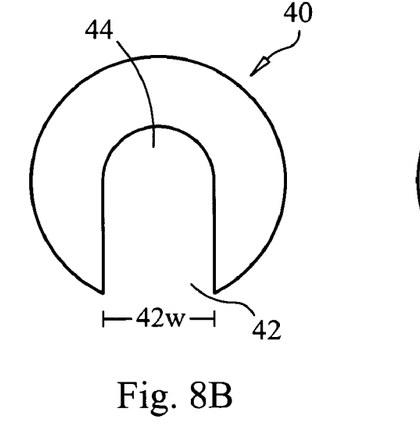
FIG. 8B shows a top or superior view of the spacer shown in FIG. 8A.
Figure 8C:
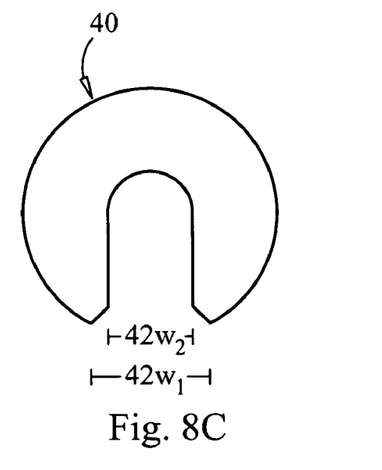
FIG. 8C shows an alternative embodiment of the spacer of FIG. 8B.

FIG. 8A illustrates an anterior view of spacer 40 and FIG. 8B shows a top or superior view of the spacer 40 shown in FIG. 8A. Both views show the opening 42 formed in the anterior portion of the ring-shaped spacer 40. Opening 42 may be in the form of a slot or gap or other separation that provides an opening that joins the exterior of the spacer 40 with the central opening 44. The width 42$w$ of opening 42 may be just slightly greater than the diameter of shaft or column 20 to allow spacer 40 to be slid over shaft/column 20, while maintaining tolerances tight to facilitate maintenance of the spacer 40 in position around the shaft/column 20 with some frictional resistance assisting this. Alternatively, opening 42 may be provided with a significantly wider dimension 42$w$1 than the outside diameter of shaft/column 20 that bevels or tapers down to a width 42$w$2 that is just slightly greater than the diameter of shaft or column 20, as shown in FIG. 8C. The greater width at the anterior end of opening 42 facilitates guidance and alignment of spacer 40 with shaft/column 20 as it is slid over the shaft/column 20.

Figure 8D:
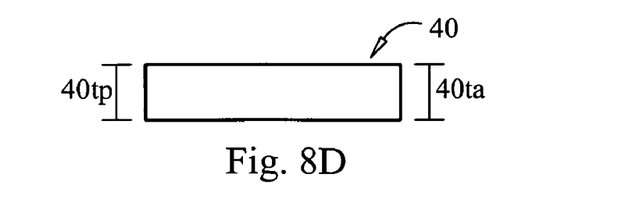
FIG. 8D illustrates a lateral side view of a spacer showing the anterior end having the same thickness as the posterior end.
Figure 8E:
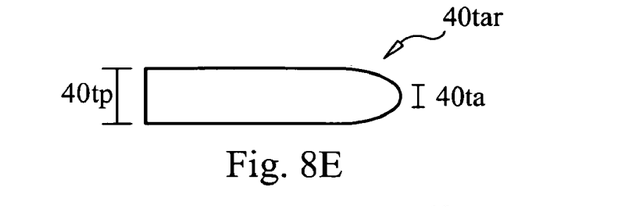
FIG. 8E shows a lateral side view of a spacer in which the anterior end is radiused or otherwise slightly reduce in thickness relative to the thickness of the remainder of the spacer.
Figure 8F:
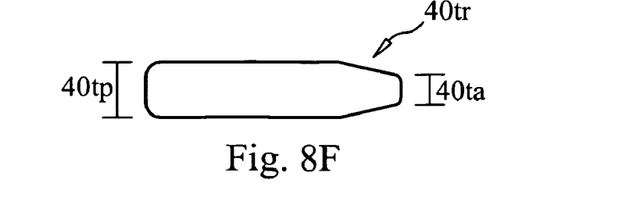
FIG. 8F shows a lateral side view of a spacer in which the anterior end portion is chamfered, beveled or otherwise tapered.

Spacer 40 may have a substantially constant thickness such that the thickness 40$tp$ at the posterior end is substantially equal to the thickness 40$ta$ at the anterior end and at all locations in between, as illustrated in FIG. 8D. Alternatively, the anterior end may be radiused 40$tar$ or have an otherwise slight reduced thickness to facilitate the insertion of spacer between surfaces 22 and 30$i$ and over shaft/column 20, as illustrated in FIG. 8E. Further alternatively, the anterior portion may be beveled or tapered 40$tr$, so that the anterior most portion is significantly less thick than the thickness of the majority of spacer 40 for making insertion easier, as shown in FIG. 8F. Typically, device 10 will be provided in a kit with a series of spacers having varying thicknesses. For example, the thickness of the spacers 40 may vary in increments of about 2 mm for use in the lumbar spine, although kits may be provided with different incremental increases in thickness of the spacers, e.g., 1 mm increments, 0.5 mm increments, 1.5 mm increments, 2.5 mm increments, or some other predetermined increment. Alternatively a kit may be provided wherein the thickness increments vary over the range. For example, the surgeon may wish to have finer resolution for varying the amount of distraction when the range of distraction nears the maximum. Thus, for example, the spacers in the lower range of amount of distraction may vary in thickness by increments of 2 mm, while the spacers in the upper range of the amount of distraction capable of being provided by the kit may vary incrementally by 1 mm each. Still further, the thinner spacers 40 may vary incrementally by 2 mm, the intermediate thickness spacers 40 may vary incrementally by 1 mm, and the thickest spacers 40 may vary incrementally by 0.5 mm, or some like arrangement. These incremental variations may also change for various factors, such as those described above (e.g., location in spine where device 10 is to be implanted, sex of patient, age of patient, etc.). In further examples, a kit of spacers 40 is provided to give the surgeon the ability to choose over a range of thicknesses from 0.5 mm to 15 mm in 0.5 mm increments, or from 0.5 mm to 15.5 mm in 1.0 mm increments or from 0.5 to 16.5 mm in 2.0 mm increments. In still further examples, a kit of spacers 40 for use in a cervical spine location may increment by thickness of 1 mm, a kit of spacers 40 for use in a thoracic spine location may increment by thickness of 2 mm, and a kit of spacers 40 for use in a lumbar spine location may increment by thickness of 3 mm. With any of these kits providing multiple spacers of varying thicknesses, such kit is provided to allow a surgeon to intra-operatively select from a range of spacer thicknesses, thus giving the surgeon flexibility as to which spacer 40 to use and thus how much overall distraction to impart.

Any of the devices described herein may be implanted adjacent to a previous fusion (e.g., implantation of device 10 between L3-L4, where a fusion has been performed between L4-L5). Further alternatively, devices 10 may be implanted at two adjacent levels, effectively forming a two-level system (e.g., implantation of device 10 between L3-L4, and implantation of another device 10 between L4-L5).

It is further noted that the outside diameter of the spacer 40 (as well as gap 42) may vary depending upon the dimensions of the shaft 20 and other components of device 10. Spacers 40 are rigid and substantially incompressible so as to maintain the original thickness 40$ta$, 40$tp$ of the spacer 40 after insertion into device 10 and placed under loading by the spine, so as to provide a predetermined amount of distraction, without variance of the thickness of spacer 40 after placed under physiological loading.

Figure 9A:
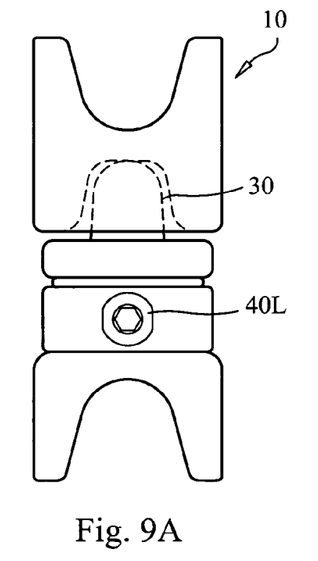
FIG. 9A is a posterior view of another embodiment of a device according to the present invention.
Figure 9B:
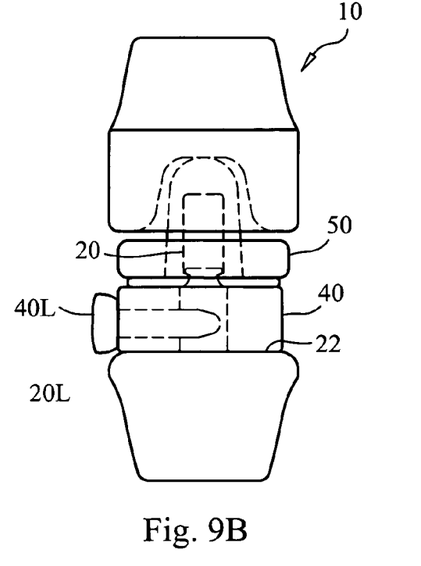
FIG. 9B is a lateral view of the device shown in FIG. 9A.

FIGS. 9A and 9B show posterior and lateral illustrations, respectively, of device 10 employing a locking mechanism 40L,20L to ensure securement or locking of spacer 40 in its intended location. As noted above with regard to FIG. 4B, shaft or column 20 may be provided with an opening 20L that forms a part of locking mechanism 40L,20L for locking/securing spacer 40 in its intended position. In the embodiment shown in FIGS. 9A and 9B, locking mechanism 40L,20L includes a threaded screw 40L and opening 20L includes mating threads along the inner wall thereof. Accordingly, after placement of collar 40 between telescoping member 30 and surface 22 and aligning screw 40L (being positioned through an opening in spacer 40) with opening 20L, screw 40L can be torqued into opening 20L to secure spacer 40 to shaft/column 20. Thus, locking mechanism 40L,20L prevents spacer 40 from "spitting out" of its location, as it may undergo shear or lateral forces during movements of the vertebrae between which device 10 is implanted. The mating thread arrangement just described is only one example of a locking mechanism that may be provided, as alternative locking mechanisms may be employed. For example, 40L may be a rod having a distal end that expands inside of opening 20L when a proximal portion of 40L is turned, in the manner of an expanding bolt. In this case opening 20L may be threaded, but does not necessarily need to be. Further optionally, opening 20L may have a smaller diameter in a posterior portion than in an anterior portion, to form a ledge or shoulder which further prevents the expanded portion of the bolt from sliding back out of opening 20L. Another alternative example is to provide one of shaft 40L and opening 20L with balls that extend radially outwardly (when on shaft 40L) or inwardly (when on inside wall of opening 20L) and wherein mating concavities or other depressions are provided on the other component, such the locking mechanism is configured as a ball detent mechanism, wherein when shaft 40L is inserted into opening 20L and the balls and depressions align, the balls move into the depressions and prevent shaft 40L from sliding back out of opening 20L. Another alternative locking mechanism is to configure spacer 40 to form a snap fit with shaft 20 like that currently used to fix a tibia insert in a tibia tray when performing a total knee replacement. Other alternative locking mechanisms may be substituted, as would be apparent to one of ordinary skill in the mechanical arts.

Figure 10A:
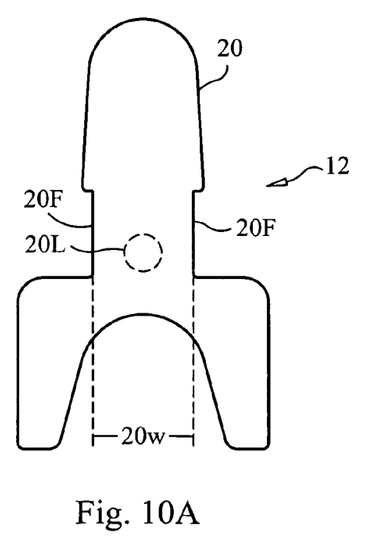
FIG. 10A illustrates an inferior mount body having a column or shaft that has flats on lateral portions of the column or shaft.

Shaft/column 20 may be configured to facilitate alignment of the components of the locking mechanism 40L,20L. For example, shaft/column 20 may be provided with flats 20F on the lateral sides thereof as illustrated in the posterior view of FIG. 10A. In this arrangement, only the lateral sides of column/shaft 20 have flats formed therein, as the remainder of the shaft/column remains the same as in previous embodiments and is curved, as in the shape of a cylinder, bell-shaped or conical-shaped. Accordingly, the ability of telescoping member to rotate about shaft/column 20 is not significantly impeded. Flats 20F may extend the entire length of the column/shaft 20 or may extend over only a portion of the column, the inferior portion where spacer 40 is intended to be fitted. Flats 20F may be provided on shaft/column even in embodiments where locking mechanism 40L,20L is not provided, as flats 20F provide a greater frictional surface to engage with spacer 40 to assist in maintaining spacer 40 fixed in its intended position.

Figure 10B:
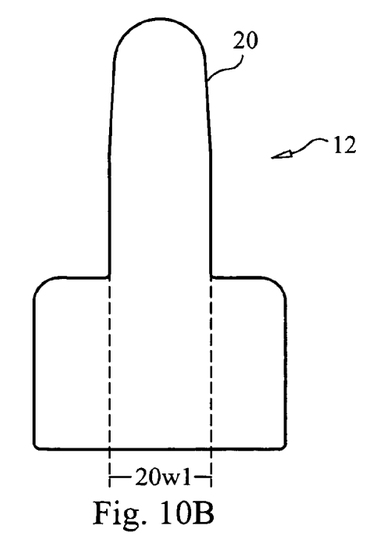
FIG. 10B is a lateral view of the inferior mount body shown in FIG. 10A.

For embodiments where a locking mechanism 40L,20L is employed, the width 42w or 42w2 of spacer 40 is only slightly greater than the distance 20w between flats 20F and may be less than the distance 20w1 between the rounded surfaces adjacent the flats measured in an anterior-posterior direction (distance 20w1 illustrated in the lateral view of FIG. 10B). With an arrangement where 42w or 42w2 is greater than 20w and less than 20w1, spacer 40 can only be fitted over shaft/column 20 in an orientation that aligns opening 20L with the opening through spacer 40 and locking member 40L when inserted through that opening.

Figure 11:
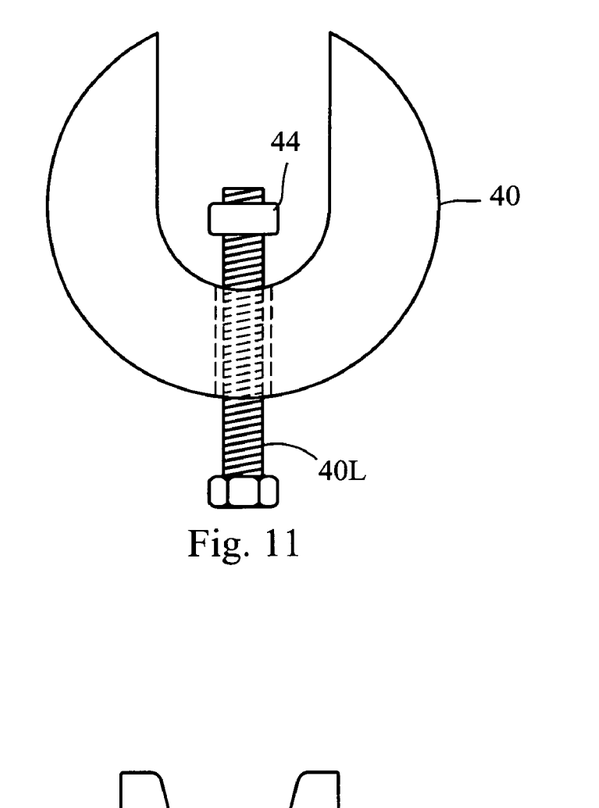
FIG. 11 illustrate a retention member for retaining a locking member with a spacer.

For further ease and simplicity, as well as safety purposes, a retaining member 44 may be mounted on the distal end portion of locking member 40L to at least loosely retain Locking member 40L inserted through the opening in spacer 40. This simplifies the implantation procedure, as the surgeon will not need to locate the locking member 40L as a separate part and then insert it through the opening of spacer 40 once spacer 40 has been placed over shaft/column 20. Even when locking member 40L is in the form of a threaded screw, it is noted that the opening through spacer 40 will typically not be threaded, and will be of a dimension large enough to allow screw 40 to slide freely therethrough, as this ensures that spacer 40 can be drawn up tight with respect to shaft/column 20 without binding issues. Retaining member 44 may be a small grommet such as a silicone grommet, for example, that can be driven against the inside surface of spacer 40 as spacer 40 is advanced toward column 20 and as locking member 40L is inserted into locking member (opening) 20L. In cases where the inner surface of spacer 40 contacts shaft/column 20 as it is secured thereto, the grommet is compressible therebetween and forms a seal with respect to the openings on both sides. Alternatively retaining member 44 may be a metal or plastic clip or other member that interacts with locking member 40L with enough resistance to prevent locking member 40L from sliding out of the opening through spacer 40 prior to engaging the locking mechanism, but with a resistance that is overcome as locking member 40L is inserted into locking member 20L so that retaining member 44 moves proximally over locking member 40L. For example, the force of retaining member 44 in contact with shaft/column 20 may be the driving force that moves retaining member 44 over locking member 40L. When locking member 40L is a threaded screw and retaining member 44 is a clip, clip 44 can be advanced proximally over the threads of threaded screw 40L as the threaded screw 40L is turned into the mating threads in opening 20L.

Implantation of device 10 is relatively simple compared to presently available products and can be performed as a minimally invasive procedure. It can be placed using a small posterior incision aligned with the spinal processes 8 between which implant 10 is to be implanted, typically where the incision is about the same length as, or less than the height of device 10 in its collapsed position (i.e., the most compact position where spacer 40 has not yet been inserted. Since typically only a single small incision is required, this greatly reduces the morbidity and time required to perform the implantation, compared to typical procedures that are currently being performed.

For a typical procedure according to one embodiment of the present invention, during pre-operative planning, the surgeon determines the size of device 10 to be used and the amount of distraction that is to be performed, such that the surgeon can determine the thickness of the spacer 40 to be used, or narrow the choices down to two or three spacers 40 covering a range of distraction distances that includes the amount of distraction thought to be needed. This pre-planning is typically facilitated by the use of radiographic imaging.

Once the pre-operative planning is complete and the patient is prepped for surgery, an incision is made through the skin and soft tissues over the location where device 10 is to be implanted between spinous processes 8. The spinous processes 8 between which device 10 is to be implanted are next distracted, such as by inserting the working ends of a distraction tool between the spinous processes 8 and then compressing the proximal ends of the distraction tool to cause the working ends to move apart, thereby distracting the spinous processes. The amount of distraction during this stage can be visualized under fluoroscopy. The amount of distraction applied at this stage will vary depending on the same factors described above, as the size of device 10 will also vary depending upon these factors. In at least one embodiment, the amount of distraction applied ranges from about 1 mm to about 2 cm, for example. In one embodiment, once the desired amount of distraction is achieved, the distraction tool can be removed from contact with the spinous processes, and, via plastic deformation, the tissues remain pliable and can thereby accommodate the placement of device 10 (in its collapsed configuration without a spacer 40) between the spinous processes 8. Then, once a spacer 40 having the desired thickness is placed in device 10, this restores the amount of distraction originally achieved by the distraction tool.

Alternatively, the distraction tool may maintain the distraction while device is inserted between the spinous processes and is configured with a spacer 40 to maintain the desired amount of distraction, after which the distraction tool can be removed.

Figure 12:
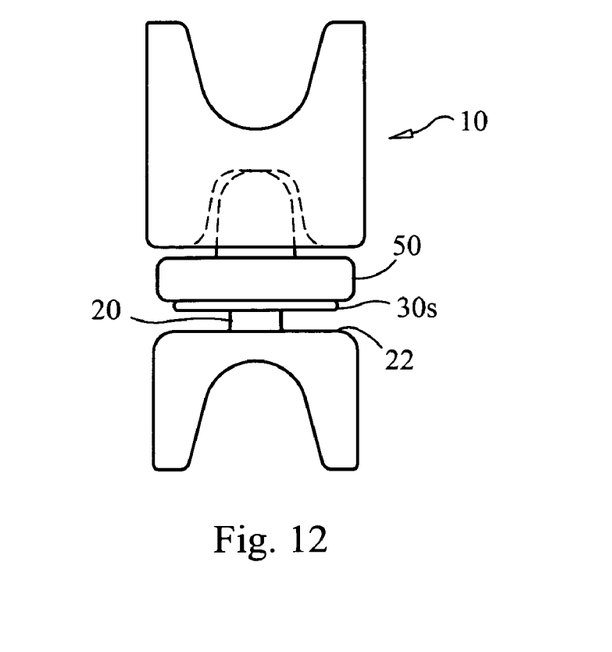
FIG. 12 illustrates a device in a compressed or collapsed configuration.

Once the spinous processes 8 have been distracted by a sufficient amount, dilation of the supraspinous ligament and interspinous ligament is performed to allow placement of device 10 in the substance of one or both of these ligaments. Device 10, in its most collapsed configuration is inserted through the incision and into the substance of the ligament(s) thereby being positioned between the spinous processes 8. FIG. 12 illustrates an example of one embodiment of device 10 in its most collapsed state, where shoulder 30s does not contact surface 22, thereby leaving a gap to facilitate subsequent insertion of spacer 50. As noted previously, in some embodiments, shoulder 30s/inferior surface 30i of telescoping member 30 will contact surface 22 in the most collapsed state. In any embodiment, the most collapsed state of device 10 includes the absence of any spacer inserted between telescoping member 30 and surface 22.

Upper surface 18 is positioned against the inferior surface of the superior spinous process 8 of the pair of spinous processes between which device 10 is being implanted. Either before, after or simultaneously with this positioning, lower surface 14 is positioned against the superior surface of the inferior spinous process of the pair of spinous processes between which device 10 is being implanted. Device 10 may be positioned between the supraspinous ligament and the interspinous ligament, or on top of the interspinous ligament, contacted against posterior portions of the spinous processes 8. Once positioned as desired, spacer 40 is inserted between the upper surface 22 of inferior mount body 12 and inferior surface 30i to contact a portion of the annular surface 30c of telescoping member 30. As spacer 40 is slid over shaft/column 20, telescoping member 30 is driven away from inferior mount body 12 by a distance equal to the predetermined thickness of spacer 40. This in turn drives superior mount body 16 away from inferior mount body 12 by the same distance, thereby distracting spinous processes 8 further by that same distance.

If the resulting overall distraction is satisfactory, in the opinion of the surgeon, then spacer 40 can be locked relative to shaft/column 20 using locking mechanism 40L,20L if device 10 is an embodiment that employs a locking mechanism 40L,20L. Otherwise, spacer 40 is left in position to be maintained by compression and frictional forces. If the overall distraction amount is unsatisfactory, i.e., either too great or too little, spacer 40 can be removed from its position between surfaces 22 and 30i and replaced by another spacer having a different (greater or lesser, depending upon the need) thickness than the first spacer. This process can be repeated until the surgeon is satisfied with the overall amount of distraction.

The amount of distraction effected will depend on different variables, including the degree of deterioration or other malady causing the patient's discomfort, the location of the vertebra/spinous processes being distracted, the age, sex, and/or species of the patient, the bone quality, etc. Typically distraction amounts may be in the range of about three to about fifteen millimeters, or about five to about fifteen millimeters, or from the height of device 10 in the collapsed configuration up to about twenty-two millimeters, for example, although these ranges may vary depending on, but not limited to the factors mentioned above. Further in this regard, it is noted that in the case where device 10 provides the desired amount of distraction without insertion of any spacer 40, implantation can be completed in this manner without installing any spacer 40 whatsoever, as device 10 will still function in the same manner as with a spacer 40. Optionally, it is possible to lock in a first distraction amount for a period of time, with device 10 in its most collapsed configuration, or with use of a first spacer 40 having a first thickness, and then extending the device 10 further by either inserting a spacer 40 in the case where none was present before, or replacing the first spacer 40 with a second spacer 40 having a thickness greater than the thickness of the first spacer 40, to increase the amount of distraction and lock in this new, greater amount of distraction. This process can be iterated as many times as desired to provide a slow and gradual widening of the space between the spinous processes 8, if desired.

In any event, once device 10 has been positioned to provide the desired amount of distraction (amount by which the spinous processes are forced apart), any distraction tools that may still be in use are removed, and the patient is closed up (including closing the incision) to complete the procedure. At a later time, the site can be re-entered to adjust the amount of distraction by changing the distance between superior 16 and inferior 12 mount bodies though removal, addition or replacement of spacer 40 according to any of the techniques described above, thereby adjusting the amount of distraction as desired.

Device 10 can also be removed, if desired, by entering the patient in the same manner described above, maintaining the amount of distraction present with one or more distraction tools, removing spacer 40 (if present) and removing device in its collapsed position. After this, the site can be again distracted by a replacement device 10, or a different procedure can be performed, or the patient can be closed without performing any further procedure.

While the present invention has been described with reference to the specific embodiments thereof, it should be understood by those skilled in the art that various changes may be made and equivalents may be substituted without departing from the true spirit and scope of the invention. For example, the device could be inverted, so that the inferior mount body performs in a manner described above with regard to the superior mount body, and the superior mount body performs in a manner described above with regard to the inferior mount body. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An interspinous implant device for distracting an adjacent pair of vertebrae while permitting relative flexion, lateral bending and side rotation motions between the vertebrae of the adjacent pair; said device comprising:
    an inferior mount body configured to mate with a spinous process of the vertebra that is inferior, relative to the pair;
    a superior mount body configured to mate with a spinous process of a spinous process of the vertebra that is superior, relative to the vertebra that is inferior;
    an intermediate member comprising a telescoping member axially slidably mounted intermediate of said inferior mount body and said superior mount body, wherein said telescoping member is slidably mounted over a superiorly extending shaft portion of said inferior mount body; and
    a spacer insertable to contact said telescoping member to drive telescoping of said telescoping member to alter a distance between said superior mount body and said inferior mount body;
    wherein upon implantation of said device between the spinous processes to contact the spinous processes, said superior mount body and inferior mount body are movable in flexion, lateral bending and side rotation, relative to one another.

2. The device of claim 1, wherein said intermediate member is axially adjustable to adjust an amount of separation between said inferior mount body and said superior mount body.

3. The device of claim 1, wherein said spacer is removable from contact with said intermediate member, wherein a second spacer having a second thickness different from a first thickness of the spacer having been removed, is insertable to alter the distance between the superior and inferior mount bodies.

4. The device of claim 1, further comprising a locking mechanism to releasably lock said spacer to said superiorly extending shaft portion.

5. The device of claim 4, further comprising a guiding feature to guide alignment of said spacer and said superiorly extending shaft portion, to align components of said locking mechanism.

6. The device of claim 5, wherein said guiding feature comprises flats on said superiorly extending shaft portion, and mating flat inner surfaces on said spacer.

7. The device of claim 1, further comprising a dampening member mounted on said intermediate member in a location to be contacted by a movement of one of said superior and inferior mount bodies prior to a limit of a range of motion of said superior or inferior mount body being reached, relative to said intermediate member.

8. A method of treating spinal disorders and associated discomfort therefrom, said method comprising:
provide an interspinous implant device for distracting an adjacent pair of vertebrae while permitting relative flexion, lateral bending and side rotation motions between the vertebrae of the adjacent pair; the device comprising an inferior mount body configured to mate with a spinous process of the vertebra that is inferior, relative to the pair; a superior mount body configured to mate with a spinous process of the vertebra that is superior, relative to the vertebra that is inferior; and an intermediate member comprising a telescoping member axially slidably mounted intermediate of said inferior mount body and said superior mount body, wherein said telescoping member is slidably mounted over a superiorly extending shaft portion of said inferior mount body; and a spacer insertable to contact said telescoping member to drive telescoping of said telescoping member to alter a distance between said superior mount body and said inferior mount body;

inserting the interspinous device between the pair of adjacent spinous processes such that a superior portion of the device contacts an inferior surface of the relatively superior spinous process of the pair, and an inferior portion of the of the device contacts a superior surface of the relatively inferior spinous process of the pair; and distracting the superior and inferior portions, relative to one another, thereby distracting the spinous processes, whereby vertebrae integral with the spinous processes retain capability of flexion, lateral bending and side rotation motions, relative to one another, after said distracting has been performed, wherein upon implantation of said device between the spinous processes to contact the spinous processes, said superior mount body and inferior mount body are movable in flexion, lateral bending and side rotation, relative to one another.

9. The method of claim 8, wherein said inserting comprises advancing the device in an anterior direction through an incision aligned with the spinous processes.

10. The method of claim 8, further comprising distracting the spinous processes with a distraction tool, prior to said inserting.

11. The method of claim 8, wherein said distracting comprises inserting the spacer intermediate of said superior and inferior portions, thereby altering a distance between the superior and inferior portions.

12. The method of claim 11, further comprising locking the spacer to a portion of the device, relative to the superior and inferior portions.

13. The method of claim 8 performed as a minimally invasive procedure.

14. The method of claim 8, wherein the device is inserted in a collapsed configuration where superior and inferior ends are in an undistracted state.

15. The method of claim 8, wherein the pair of adjacent spinous processes comprises a first pair of adjacent spinous processes, said method further comprising inserting a second interspinous device between a second pair of adjacent spinous processes such that a superior portion of the second interspinous device contacts an inferior surface of the relatively superior spinous process of the second pair, and an inferior portion of the second interspinous device contacts a superior surface of the relatively inferior spinous process of the second pair, and wherein said second pair of spinous processes includes one spinous process in common with said first pair of spinous processes.

16. The method of claim 8, wherein the pair of adjacent spinous processes comprises a first pair of adjacent spinous processes, and wherein a second pair adjacent spinous processes extends from a pair of adjacent vertebrae having been fused, and wherein said second pair of spinous processes includes one spinous process in common with said first pair of spinous processes.

* * * * *